US007597912B2

(12) United States Patent
Probasco

(10) Patent No.: US 7,597,912 B2
(45) Date of Patent: Oct. 6, 2009

(54) COMPOSITIONS AND METHODS FOR CONTROLLING A HONEY BEE PARASITIC MITE

(75) Inventor: Gene Probasco, Yakima, WA (US)

(73) Assignee: John I. Haas, Washington, DC (US)

( * ) Notice: Subject to any disclaimer, the term of this patent is extended or adjusted under 35 U.S.C. 154(b) by 0 days.

(21) Appl. No.: 11/732,504

(22) Filed: Apr. 2, 2007

(65) Prior Publication Data

US 2008/0026673 A1 Jan. 31, 2008

Related U.S. Application Data

(63) Continuation-in-part of application No. 11/396,360, filed on Mar. 31, 2006.

(51) Int. Cl.
*A61K 36/28* (2006.01)
(52) U.S. Cl. ..................................................... 424/737
(58) Field of Classification Search ........................ None
See application file for complete search history.

(56) References Cited

U.S. PATENT DOCUMENTS

| 3,615,660 | A | 10/1971 | Bavisotto et al. |
| 4,148,873 | A | 4/1979 | Owades |
| 4,170,638 | A | 10/1979 | Owades |
| 5,227,162 | A | 7/1993 | Ferrari et al. |
| 5,372,817 | A | 12/1994 | Locke et al. |
| 5,827,895 | A | 10/1998 | Nutter et al. |
| 6,096,350 | A | 8/2000 | Kemp et al. |
| 6,204,283 | B1* | 3/2001 | Black et al. ................. 514/406 |
| 6,646,014 | B2* | 11/2003 | Watkins ...................... 514/731 |
| 6,702,645 | B2* | 3/2004 | Vanderpool .................... 449/2 |
| 2001/0014346 | A1 | 8/2001 | Watkins |
| 2002/0051804 | A1* | 5/2002 | Probasco et al. ............ 424/405 |
| 2003/0060379 | A1 | 3/2003 | Souter et al. |
| 2005/0043404 | A1 | 2/2005 | Probasco et al. |
| 2005/0049230 | A1 | 3/2005 | Henrich et al. |
| 2005/0220914 | A1 | 10/2005 | Probasco et al. |
| 2006/0009122 | A1 | 1/2006 | Swanson |
| 2006/0013870 | A1 | 1/2006 | Kuhrts |
| 2007/0232188 | A1 | 10/2007 | Probasco |
| 2008/0026673 | A1 | 1/2008 | Probasco |

FOREIGN PATENT DOCUMENTS

GB 2330076 4/1999

OTHER PUBLICATIONS

International Search Report for PCT/US07/23984.
"Culpeper's Complete Herbal A book of Natural Remedies for Ancient Ills," Wordsworth Reference, pp. 134-135 (1995).
Jones, G., "Potential Control of Two-Spotted Spider Mite, Tetranychus Urticae Koch, Using Hop β-Fraction," (1998) pp. 1-165, A thesis submitted for the degree of Doctor of Philosophy of the Univeristy of London and for the Diploma of Imperial College of Science, Technology & Medicine.

(Continued)

Primary Examiner—Christopher R. Tate
Assistant Examiner—Deborah A. Davis
(74) Attorney, Agent, or Firm—Edwards Angell Palmer & Dodge LLP; Jeffrey D. Hsi; Melissa Hunter-Ensor, Esq.

(57) ABSTRACT

As described below, the present invention provides methods and compositions for controlling a honey bee parasitic mite. In addition, the invention features compositions useful for the treatment or prevention of a parasitic mite infestation in a honey bee hive.

8 Claims, 5 Drawing Sheets

OTHER PUBLICATIONS

Jones et al., "Repellant and Oviposition-Deterring Effects of Hop-Beta Acids on the Two-Spotted Spider Mite Tetranychus Urticae," Pesticide Science, Vol. 47, No. 2, pp. 165-169 (1996).

Losel, et al., The Potentional of Semidochemicals for Control of Phorodon Hummuli (Homoptera: Aphididae), Pesticide Science, Vol. 48, No. 4, pp. 293-303 (1996).

* cited by examiner

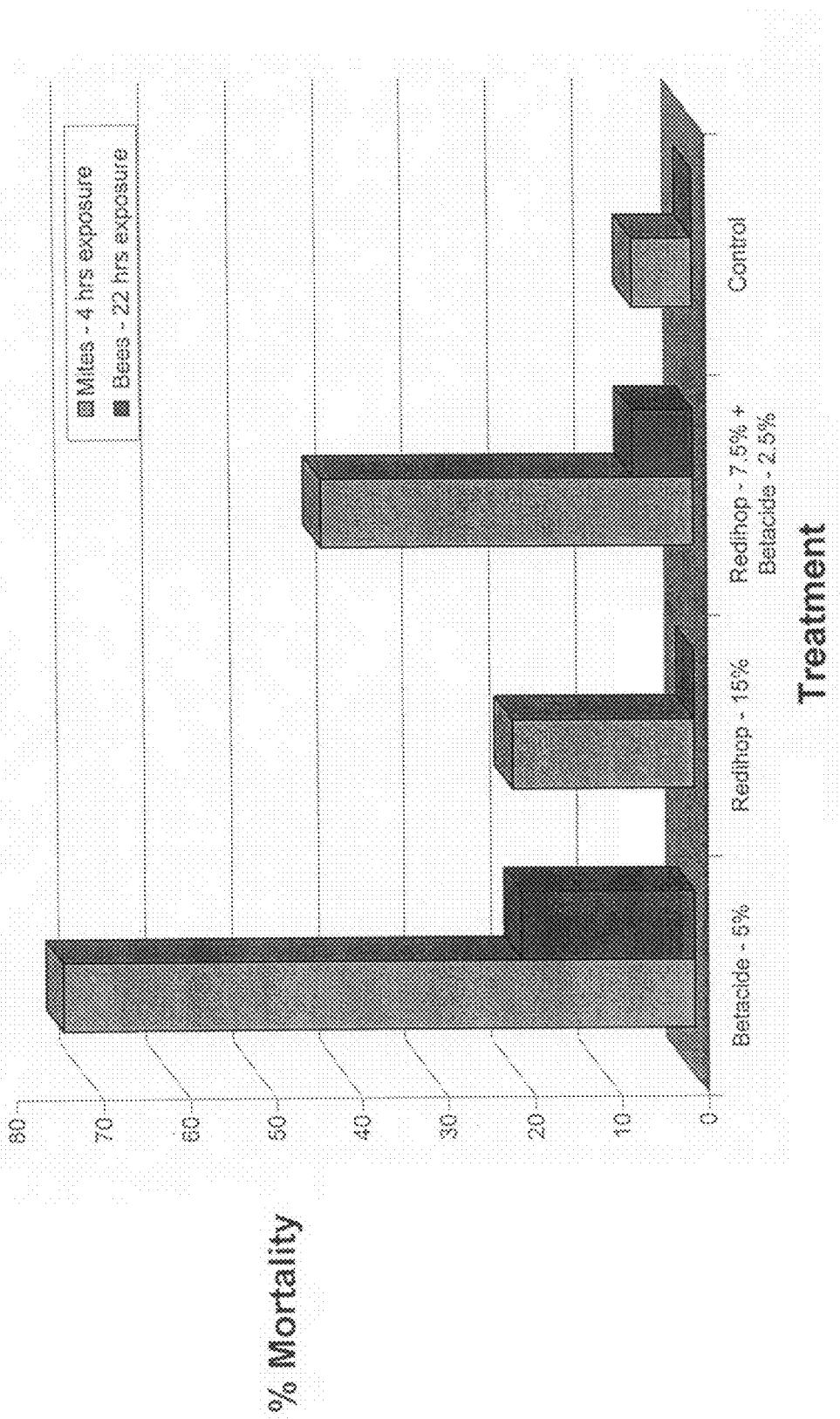

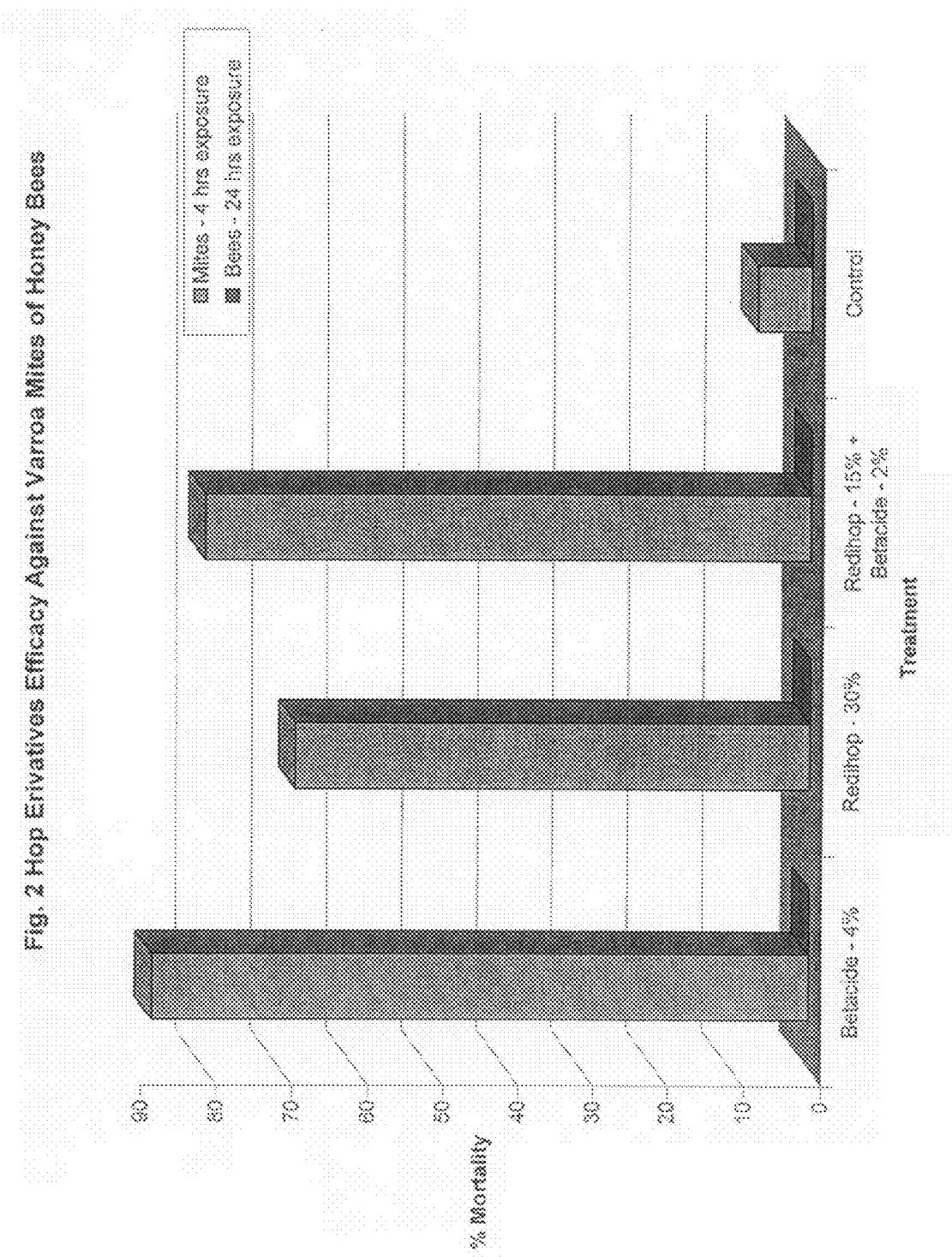

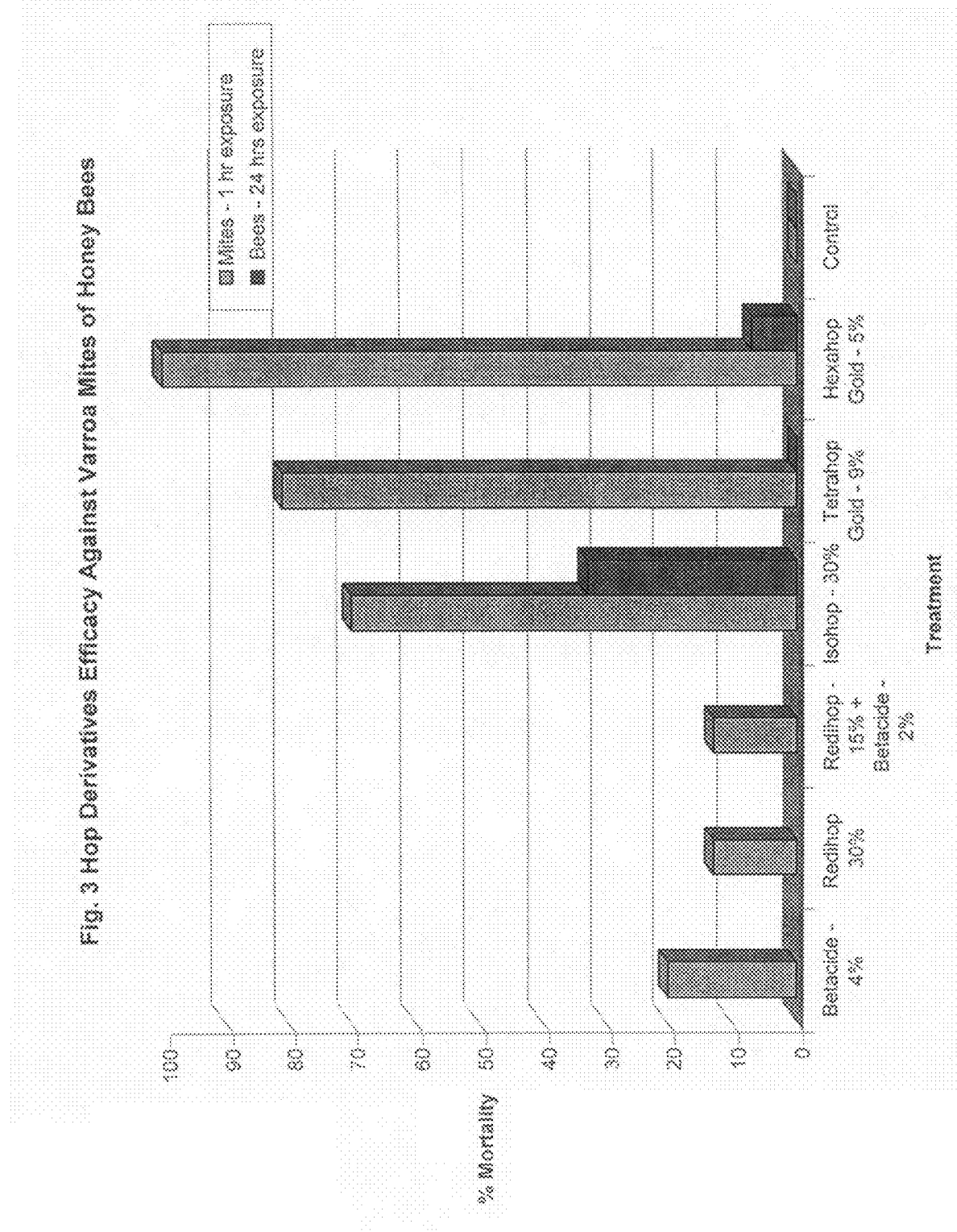
Fig. 3 Hop Derivatives Efficacy Against Varroa Mites of Honey Bees

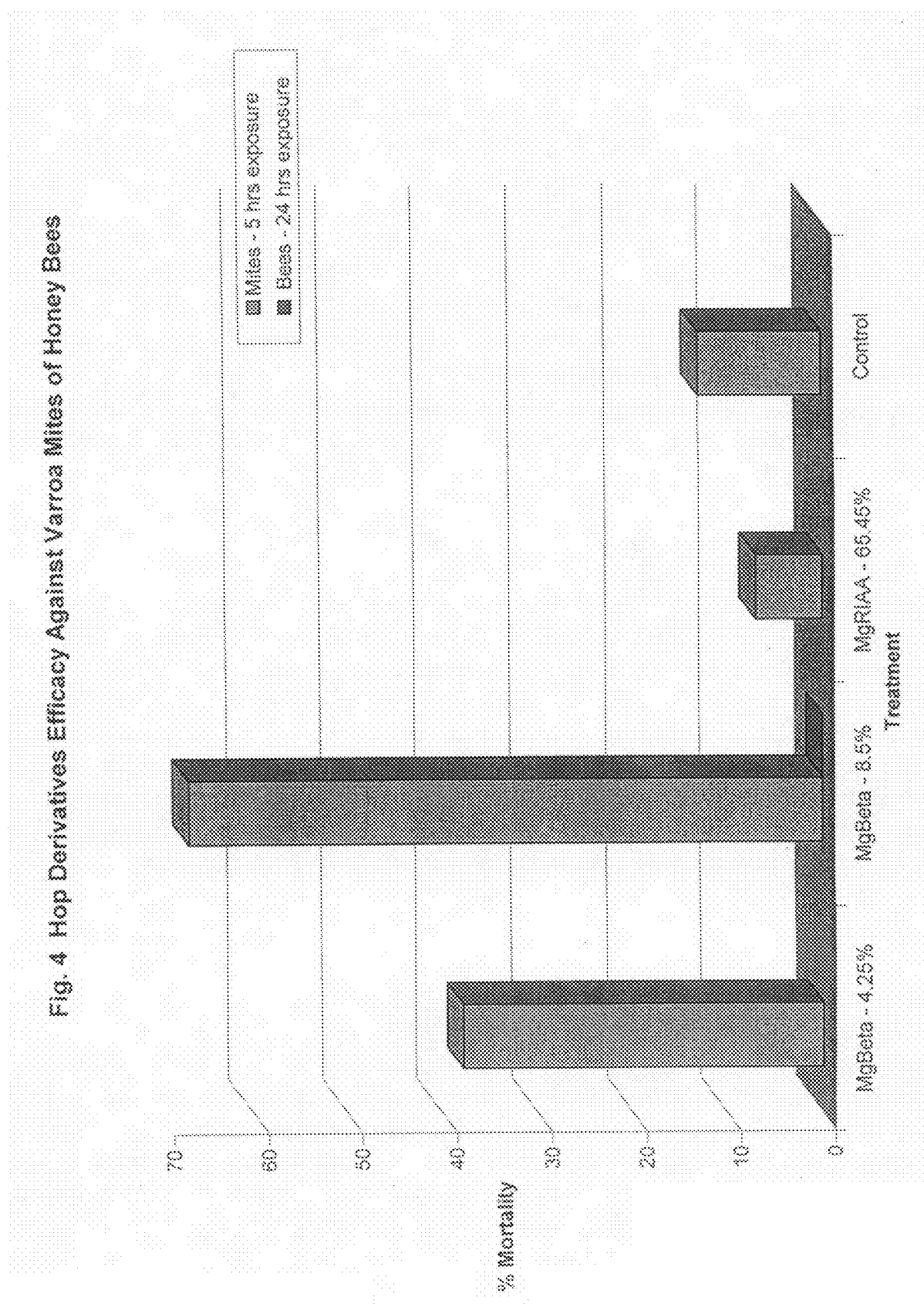

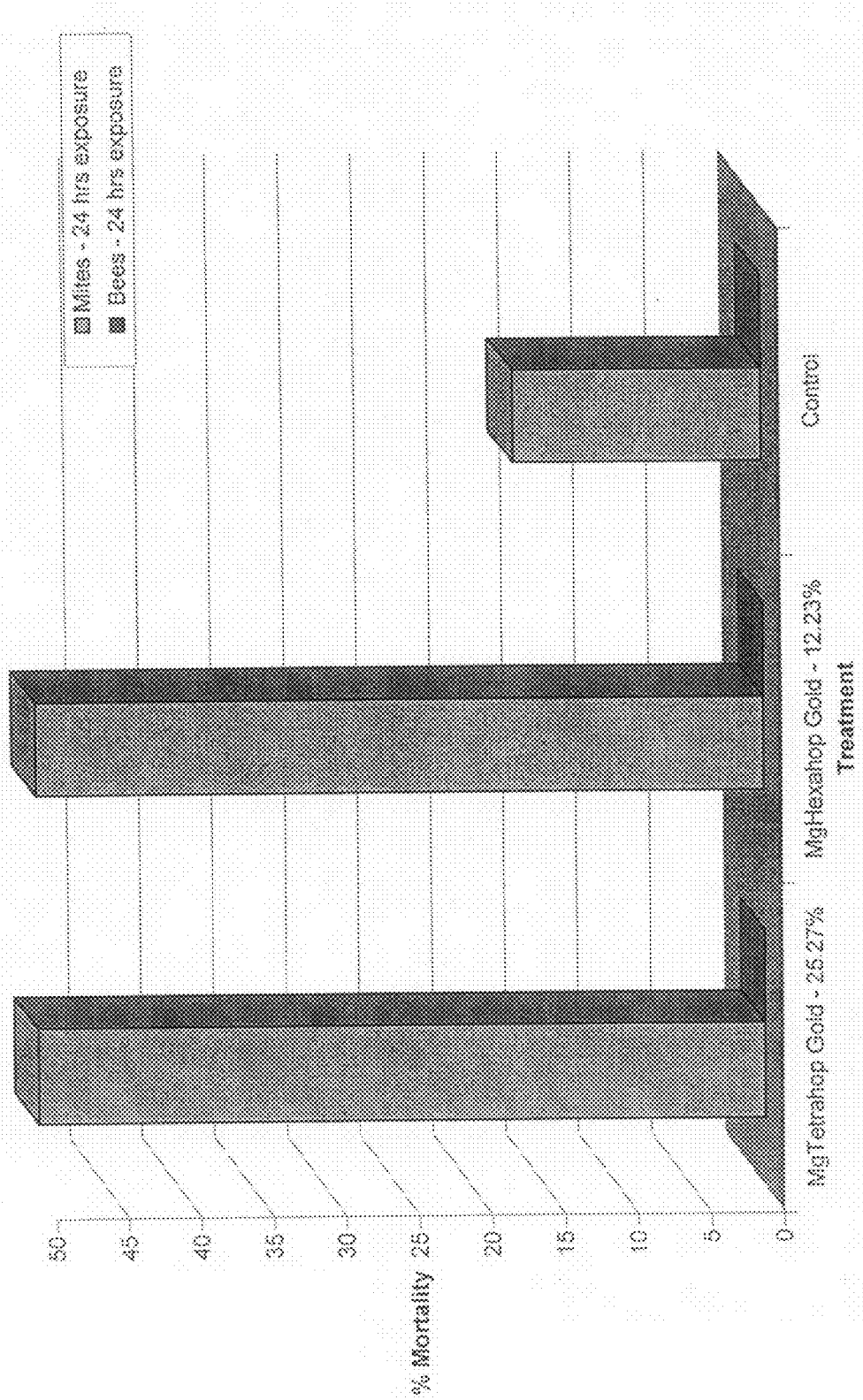

US 7,597,912 B2

COMPOSITIONS AND METHODS FOR CONTROLLING A HONEY BEE PARASITIC MITE

CROSS-REFERENCE TO RELATED APPLICATION

This application is a continuation in part of U.S. Utility application Ser. No. 11/396,360, filed on Mar. 31, 2006, the entire contents of which are incorporated herein by reference.

BACKGROUND OF THE INVENTION

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*. *Varroa* mites parasitize pupae and adult bees and reproduce in the pupal brood cells. The mites use their mouths to puncture the exoskeleton and feed on the bee's hemolymph. These wound sites in the exoskeleton harbor bacterial infections, such as *Melissococcus pluton*, which causes European foulbrood. In addition, to their parasitic effects, *Varroa* mites are suspected to act as vectors for a number of honey bee pathogens, including deformed wing virus (DWV), Kashmir bee virus (KBV), acute bee paralysis virus (ABPV) and black queen cell virus (BQCV), and may weaken the immune systems of their hosts, leaving them vulnerable to infections. If left untreated *Varroa* infestations typically result in colony-level mortality. Maintaining a supply of strong honey bee colonies available for pollination is essential for the sustained production of farm crops worth more than $14 billion to U.S. agriculture. During the winter of 2004-2005, an estimated 40% of the honey bee colonies in the U.S. were weakened or collapsed due to *Varroa* infestation. Current methods of treating *Varroa* infestations are proving to be ineffective as the mites develop resistance to existing miticides. In addition, the use of such miticides may introduce injurious chemicals into honey that is intended for human consumption. New compositions and methods for treating or preventing *Varroa* mite infestations are urgently required. Desirably, such compositions would include only natural ingredients that pose no risk to human health.

SUMMARY OF THE INVENTION

As described below, the present invention features methods and compositions for controlling a honey bee parasitic mite or for the treatment or prevention of a parasitic mite infestation in a honey bee hive.

In general, the invention provides a method of controlling a honey bee parasitic mite (e.g., *Varroa* mite, tracheal mite). The method involves contacting the parasitic mite with an effective amount of a composition comprising a hop derivative (e.g., alpha acid, beta acid, or combination thereof), thereby controlling a honey bee parasitic mite. In one embodiment, the contacting of the mite occurs while the mite is in contact with a honey bee (e.g., honey bee egg, larva, or pupa).

In a related aspect, the invention provides a method of treating or preventing a parasitic mite infestation of a honey bee hive. The method involves contacting the hive with an effective amount of a composition comprising a hop derivative, thereby treating or preventing a parasitic mite infestation in a honey bee hive.

In another aspect, the method herein further include those wherein the hive or mite is identified as in need of the treatment or prevention protocols delineated herein.

In another aspect, the invention provides a composition for treating or preventing a mite infestation, the composition comprising an effective amount of a hop derivative in a suitable form for delivery to a mite. Suitable forms include, for example, any one or more of a liquid, a powder, an oil, an emulsion, a paste, a capsule, a vapor, or any other form capable of delivering a hop derivative to a *Varroa* mite in contact with a honey bee or honey bee hive. If desired, the composition further comprises a carrier.

In yet another aspect, the invention features a composition for treating or preventing a mite infestation, the composition comprising an effective amount of a hop derivative in a suitable form for delivery to a mite. In one embodiment, the hop derivative is an alpha acid, beta acid, or combination of an alpha and a beta acid. In another embodiment, the hop derivative is a metal alkali salt or earth alkaline metal salt of hop acid. In other embodiments, the composition comprises at least 2.5%, 5%, 7.5%, 15% alpha acids, beta acids, or a combination of alpha and beta acids. In another embodiment, the form is selected from the group consisting of a liquid, a powder, an oil, an emulsion, a capsule, and a vapor. In yet another embodiment, the composition further comprises a carrier (e.g., any one or more of maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, and hypomellose). In yet other embodiments, the composition is a powder having particles of a size selected from the group consisting of 1 μm, 5 μm, 10 μm, 25 μm, 50 μm, 75 μm, 100 μm, 150 μm, 200 μm, 500 μm, 1 mm, 2 mm, or 5 mm, such as a powder prepared by spray drying.

In yet another embodiment, the invention provides a miticide composition comprising an effective amount of a hop acid alkali metal salt or hop acid alkaline earth metal salt and a carrier in a suitable form for delivery to a mite. In one embodiment, the hop acid alkali metal salt is a sodium, potassium, or lithium salt. In another embodiment, the hop acid alkaline earth metal salt is calcium or magnesium. In yet another embodiment, the carrier is selected from the group consisting of maltodextrin, cluster dextrin, corn starch, corn syrup solids, glucose, cyclodextrin, arabic gum, calaginan, inuline, rosin, partially hydrogenated soybean oil, cellulose, hydroxymethy cellulose, hydroxyethyl cellulose, hydroxypropyl cellulose, and hypomellose. In still other embodiments, the composition is spray dried to form particles of a size selected from the group consisting of 1 μm, 5 μm, 10 μm, 25 μm, 50 μm, 75 μm, 100 μm, 150 μm, 200 μm, 500 μm, 1 mm, 2 mm, and 5 mm in size. In still other embodiments, the hop acid to carrier ratio is selected from the group consisting of 1:2, 1:5, 1:10, 1:20, 1:50, and 1:100. In other embodiments, the hop acid maintains miticidal activity for at least about six months, nine months, twelve months, eighteen months, twenty-four months, or thirty-six months. In still other embodiments, the hop acid maintains stability for at least about six months, nine months, twelve months, eighteen months, twenty-four months, or thirty-six months.

In yet another aspect, the invention provides a controlled release composition for treating or preventing a parasitic mite infestation, the composition comprising an effective amount of a hop derivative in a suitable form for delivery to a honey bee parasitic mite.

In yet another aspect, the invention provides a miticide delivery device, the device comprising a composition of any previous aspect. In one embodiment, the device is selected from the group consisting of a strip (e.g., membranes, paper, plastic, or polymer strip), controlled release strip, tablet, reservoir, polymer disc, evaporation device, fiber, tube, polymeric block, membrane, pellet, tray, and microcapillary. If desired, any of these devices can be formulated in a biodegradable form.

In yet another aspect, the invention provides a hive comprising a composition of any previous aspect.

In yet another aspect, the invention provides a honey bee product produced in a hive of any previous aspect. Honey bee products include, but are not limited to, honey, honey comb, and bees wax.

In yet another aspect, the invention provides a kit for the treatment or prevention of an parasitic mite infestation, the kit comprising an effective amount of a hop derivative in a form suitable for delivery to a site of infestation (e.g., a bee hive or a bee). In one embodiment, the kit features directions for use in a method of the invention.

In yet another aspect, the invention provides a method of identifying a hop derivative that disrupts a biological function of a honey bee parasitic mite. The method involves contacting the parasitic mite with a test composition comprising a hop derivative; and assaying a parasitic mite biological function. In one embodiment, the test composition disrupts a parasitic mite biological function (e.g., kills or incapacitates the parasitic mite or reduces parasitic mite reproduction). In another embodiment, the method further includes the steps of contacting a honey bee with the test composition; and assaying a honey bee biological function. In yet another embodiment, the method identifies a test compound that does or does not disrupt a honey bee biological function. In another embodiment, the method identifies a test compound that kills a honey bee.

In a related aspect, the invention provides a method of identifying a hop derivative that does not disrupt a biological function of a honey bee. The method involves contacting the honey bee with a test composition comprising a hop derivative; and assaying a honey bee biological function. In one embodiment, the method identifies a test compound that does or does not disrupt a honey bee biological function. In another embodiment, the test compound kills a honey bee.

In various embodiments of any previous aspect, a hop derivative is an alpha acid or a beta acid. In other embodiments of a previous aspect, a composition of the invention contains an alpha acid, a beta acid, or a combination thereof, wherein the amount of alpha or beta acid in the composition ranges between 1% and 100%, where the bottom limit of the range is any integer between 1 and 99% and the upper limit of the range is any integer between 2% and 100%. Exemplary amounts of an alpha, a beta, or a combination thereof include at least 1%, 2.5%, 5%, 7.5%, 10%, 12%, 15%, 20%, 25%, 35%, 40%, 50%, 60%, 75%, 85%, 90% or 95% in a composition. In one particular embodiment, the composition comprises at least 1%, 2%, 2.5%, 3%, 5%, or 10% beta acid and at least 1%, 2%, 3%, 5%, 6%, 7.5%, 8%, 9%, 10%, 12%, or 15% alpha acids. In one embodiment of any of the above aspects, the contacting disrupts a biological function of a mite. Exemplary biological functions include any one or more of respiration, neural activity, locomotion, reproduction, or any other physiological activity required for mite survival. In one embodiment, the contacting kills the mite.

In still other embodiments of any previous aspect, the hop acid alkali metal salt is a sodium, potassium, or lithium salt. In other embodiments of any previous aspect, the hop acid alkaline earth metal salt is calcium or magnesium. In other embodiments of any previous aspect, the carrier is selected from the group consisting of maltodextrin, cluster dextrin, corn starch, corn syrup solids, glucose, cyclodextrin, arabic gum, calaginan, inuline, rosin, partially hydrogenated soybean oil, cellulose, hydroxymethy cellulose, hydroxyethyl cellulose, hydroxypropyl cellulose, and hypomellose. In still other embodiments of any previous aspect, the composition is spray dried to form particles of a size selected from the group consisting of 1 µm, 5 µm, 10 µm, 25 µm, 50 µm, 75 µm, 100 µm, 150 µm, 200 µm, 500 µm, 1 mm, 2 mm, and 5 mm in size. In still other embodiments, the hop acid to carrier ratio is selected from the group consisting of 1:2, 1:5, 1:10, 1:20, 1:50, and 1:100. In other embodiments, the hop acid maintains miticidal activity for at least about six months, nine months, twelve months, eighteen months, twenty-four months, or thirty-six months. In still other embodiments, the hop acid maintains stability for at least about six months, nine months, twelve months, eighteen months, twenty-four months, or thirty-six months.

In yet other embodiments, the composition of the invention is a controlled release composition wherein the hop derivative is released over the course of at least one week to 12 months. For example, the hop derivative is released over at least 5, 10, 14, 28, 36, 41, or 48 days; or is released over the course of 1, 2, 4, 6, 8, 10 or 12 weeks, or even for as long as 5, 6, 9, or 12 months.

Other features and advantages of the invention will be apparent from the detailed description, and from the claims.

DEFINITIONS

By "acarid" is meant an arachnid of the order Acarina, which includes mites and ticks.

By "alpha acid" is meant an organic acid derived from a hop plant (*Humulus lupulus*) having structural homology to a humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to a lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydro hulupones.

By "biological function" is meant any physiological or behavioral activity of an organism. Exemplary biological functions include reproduction, respiration, neural activity, locomotion. Honey production is a biological function that is specific to a honey bee.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "contacting" is meant touching, associating with, or having proximity to a composition. For example, a hop derivative may contact a hive either inside or outside of the hive structure.

By "controlled release" is meant released over the course of hours, days, weeks, or months.

By "controlling a parasitic mite" is meant inhibiting mite survival or reducing, slowing, or stabilizing the growth of a mite population.

By "comb" is meant sections of hexagonal bee wax cells that are used to rear honey bee progeny ("brood") and store honey and pollen.

By "effective amount of a miticide" is meant an amount effective to disrupt a mite biological function.

By "hive" is meant a structure that contains a bee colony. A modern box hive typically includes a bottom board, cover, and one or more boxes, stacked one above the other. Inside, each box contains a series of movable frames of comb or foundation held in a vertical position a bee space apart.

By "honey bee" is meant a Hymenopteran insect of the genus *Apis*. The term "honey bee" is not limited to the adult form of the insect, but encompasses all honey bee developmental stages, including but not limited to egg, larva, and pupa. Exemplary honey bee species include *Apis mellifera* and *Apis cerana*.

By "honey bee colony" is meant a community of bees. Honey bee colonies may occur in the wild or may be maintained by bee keepers.

By "honey bee parasitic mite" is meant any acarid that parasitizes a honey bee or infests a honey bee hive. Exemplary honey bee parasitic mites include *Varroa* mites and tracheal mites.

By "hop derivative" is meant any molecule that naturally occurs in hops (*Humulus lupulus*) and chemical derivatives thereof. Hop derivatives (e.g., alpha acids, beta acids) may be purified from hops or may be chemically synthesized.

By "infestation" is meant the colonization of a site or the parasitization of an organism by a pest.

By "miticide" is meant an agent that inhibits a biological function of a mite.

By "miticidal activity" is meant any activity that inhibits the growth, reproduction, or survival of a mite or other acarid.

By "preventing a mite infestation" is meant reducing the success that a mite infestation will be established in an *Apis* colony.

By "treating a mite infestation" is meant reducing, stabilizing, or slowing the growth of a mite population in an *Apis* colony.

BRIEF DESCRIPTION OF THE DRAWINGS

FIG. 1 is a graph showing *Varroa* mite and honey bee mortality at four hours and twenty-two hours respectively in response to hop product exposure at the indicated concentrations.

FIG. 2 is a graph showing *Varroa* mite and honey bee mortality four hours and at twenty-four hours respectively in response to hop product exposure at the indicated concentrations.

FIG. 3 is a graph showing *Varroa* mite and honey bee mortality at one hour and twenty-four hours respectively in response to hop product exposure at the indicated concentrations.

FIG. 4 is a graph showing *Varroa* mite mortality at five hours and adult honey bee mortality at twenty-four hours in response to hop product exposure at the indicated concentrations. MgBeta denotes magnesium salts of beta acids. RIAA denotes rhoisoalpha acids.

FIG. 5 is a graph showing *Varroa* mite and honey bee mortality at twenty-four hours in response to hop product exposure at the indicated concentrations.

DETAILED DESCRIPTION OF THE INVENTION

The present invention is directed to methods and compositions to control acarids and other related species of the family Varroidae. The invention is based, in part, on the discovery that naturally occurring components of hops are useful for the prevention or treatment of a *Varroa* mite infestation.

*Apis*

Honey bees are insects that pass through four life stages: the egg, larva, pupa and adult. Adult bees belong to one of three castes: queen, worker, or drone. The queen bee is the only female in the colony that is capable of reproduction and is responsible for all egg production. The worker bees are non-reproductive females who gather honey and care for the queen's progeny, or "brood." The drones are male bees that mate with the queen. The life cycle, from egg to adult bee, takes twenty-one days for worker bees and twenty-four days for drones. The queen bee lays each egg in a single cell of the comb. The egg generally hatches into a larva on the fourth day, which continues its development within the cell. On the ninth day the cell with the developing larva is capped with wax and the larva undergoes pupal metamorphosis. On day twenty-one, a new adult worker bee emerges.

Acarids

Acarids are small parasitic arachnids that act as parasites on a variety of plants and animals, including honey bees. Parasitic mites that prey on honey bees include *Varroa* mites (e.g., *Varroa destructor, Varroa jacobsoni*) and tracheal mites (e.g., *Acarapis woodi*) Tracheal mites are microscopic mites that inhabit the respiratory tubes of bees. *Varroa* mites are ectoparasites that feed on bee hemolymph, and infest wild and domestic honey bee colonies. *Varroa* mite reproduction begins when the adult female mite enters a brood cell shortly before it is capped. Drone brood, which is reared in larger cells than worker brood, is preferentially targeted for mite infestation. The female mite feeds on the larval hemolymph prior to depositing her eggs. The *Varroa* eggs eclose under the sealed cell, and the developing mites feed on the bee pupa. The first egg laid by the female *Varroa* develops into a male. Subsequent eggs develop into females that mate with their brother. The mated female mites along with their mother are released from the capped cell when the bee emerges. The female mites typically attach to adult bees between the abdominal segments or between body regions, where they feed on the bees' hemolymph. Adult bees serve as intermediate hosts and as a means of transport to new sites of infestation.

Desirably, miticides used in acarid control should address the following four needs: i) should disrupt a physiological function required for mite survival; ii) should cause no adult bee mortality; iii) should have no adverse effects on human bee keepers or honey intended for human consumption; and iv) should be capable of delivery into the hive.

Mite Control

Products used to control honey bee parasitic mite infestation reduce, stabilize, or slow the growth of a mite population in a hive or inhibit the growth, survival, reproduction, or other biological function of a honey bee parasitic mite. Preferably, the miticide kills the mite. Methods for measuring parasitic mite infestation are known in the art. A number of parameters can be indicative of the level of infestation present in a bee colony: the number of mites present in a sample of bees from an infested hive can be used as one measure of the level of infestation present in the hive; bees reared in a hive having an active infestation are on average smaller than bees reared in a hive without infestation; thus, bee size or weight can be used as another measure of infestation; the amount of honey produced in an infected hive may be less than that produced in a healthy hive; accordingly, honey production could serve as yet another measure of the level of infestation; and finally, severe infestations result in complete loss of colonies. Thus, loss of colonies can be a measure of the level of infestation present in the hive. In one embodiment, a miticide of the invention reduces the level of infestation in a hive by at least 10%, 25%, 50%, 75% or even by 100%. In another embodiment, a miticide of the invention induces at least 50%, 60%, or 70% mite lethality. Preferably, the miticide induces 75%, 80%, 90%, or even 95% or 100% mite lethality. Screening methods are used to identify concentrations of hop derivatives that will be lethal to a mite (e.g., induce at least 70% mite lethality) while minimizing lethal effects on adult bees.

Alternatively, a miticide of the invention inhibits mite reproduction. Preferably, the miticide reduces mite reproduction by at least 25%, 50%, 75% or 100%. In another approach, the miticide disrupts a biological function required for acarid locomotion; such treatment allows the mite to be trapped, drowned, isolated, or otherwise removed from an area.

Miticide Screening

Commercial products that are currently being used to control mite infestation can be lethal to adult bees when administered at high concentrations, can have adverse effects on human bee keepers, and may contaminate honey intended for human consumption. Conventional miticides include Tau-Fluvalinate (a synthetic-pyrethroid compound used as a selective contact and stomach poison) and Coumaphos (a systemic organic phosphate) used on animals to control lice, ticks and mites. In contrast to conventional miticides, compositions of the invention contain safe natural products derived from hops. Hops have been used for centuries to flavor beer; thus, formulations comprising hop derivatives are generally safe. Miticidal compositions of the invention will not adversely affect human bee keepers or honey intended for human consumption.

Miticides of the invention contain concentrations of hop derivatives that have few or no adverse effects on honey bees during any of their life stages, but are effective in killing or disrupting the biological functioning of a mite. As reported herein, beta acids, a hop derivative, delivered at 4% concentration killed 87% of exposed mites after four hours while causing 0% lethality in adult bees. In one approach, mites are exposed to varying concentrations of hop derivatives to identify those concentrations that kill 50% to 100% of the exposed mite. Adult honey bees are then exposed to concentrations of hop derivatives having miticidal activity to identify those that have a minimal effect on honey bee survival. Preferably, at least 75%, 80%, 85%, 90%, 95%, or 100% of adult bees will survive following exposure to a miticidal composition. In a similar approach, the effect of hop derivatives on mite and honey bee reproduction is assessed. Screening assays are used to determine the concentration of a miticide that reduces the number of eggs laid by the female mite, reduces the number of eggs that hatch, or reduces the number of mites that grow to reproductive maturity; preferably, the reduction is by at least 25%, 50%, 75%, 85%, 95% or 100%.

Hop Derivatives

A hop derivative is a compound that occurs naturally in a hop plant (*Humulus lupulus*) or is chemically derived (either through natural biosynthetic processes (e.g., living organism metabolism (e.g., mammal, plant, bacteria)) or by synthetic processes using human intervention (e.g., chemical synthesis). Compositions of the invention include one or more compounds derived from hops. Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adlupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include beta acids, hexahydrobeta acids, rhoisoalpha acids, isoalpha acids, tetrahydroisoalpha acids, hexahydroisoalpha acids, magnesium salts of rhoisoalpha acids and magnesium salts of beta acids. Compositions comprising hop derivatives are also available commercially. John I. Haas, Inc. products containing hop derivatives include Betacide, Redihop®, Isohop®, Tetrahop Gold®, Hexahop Gold®, MgRIAA and MgBeta. The active ingredients in these products are beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids (MgBeta), respectively. For convenience, the identities of these products are also listed in Table 1. These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by carbon-dioxide supercritical (temperature/pressure) extraction. The extract may then be further evaporated and thus concentrated to yield by means of air drying, spray drying, vacuum oven drying, fluid-bed drying or freeze-drying, the extract product.

Crude extracts are tested for miticidal activity as described herein. Further fractionation of a positive lead extract having miticidal activity is necessary to isolate chemical constituents responsible for the observed effect. Thus, the goal of the extraction, fractionation, and purification process is the careful characterization and identification of a chemical entity within the crude extract that disrupts a mite biological function. Methods of fractionation and purification of such heterogeneous extracts are known in the art. If desired, compounds shown to be useful as miticides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$salts. This invention also envisions the quaternization of any basic nitrogen-containing groups of the compounds disclosed herein. Water or oil-soluble or dispersible products may be obtained by such quaternization.

In some embodiments, miticidal compositions of the invention include water soluble hop acid alkali metal salts (e.g., sodium, potassium, lithium salts) and water insoluble hop acid alkaline earth metal salts (e.g., calcium, magnesium) having increased stability. These hop acid alkali metal salt (e.g., sodium, potassium, lithium salts) and water insoluble hop acid alkaline earth metal salt (e.g., calcium, magnesium) compositions are advantageously stable relative to hop acids produced by conventional methods, which are susceptible to degradation due to heat, light, and acid catalysis. Compositions of the invention remain stable under conditions that induce the degradation of other conventional hop acids. In particular, after 6 months to 1 year of storage, the compositions of the invention are expected to retain at least about 50%, 60%, 75%, 80%, or preferably at least about 90%, 95% or even 100% of the hop acids present at the time of application. Surprisingly, hop β acid crystals are also resistant to degradation and exhibit increased stability. Accordingly, hop β acid crystals are also useful in the compositions and methods of the invention.

Water soluble hop acid alkali metal salts (e.g., sodium, potassium, lithium salts) and water insoluble hop acid alkaline earth metal salts (e.g., calcium, magnesium) are typically present in a diluent or carrier at levels ranging from about 0.1% to about 95%. The methods herein contemplate administration of an effective amount of compound or compound composition to achieve the desired or stated miticidal effect. Preferably, the amount of active ingredient (e.g., hop acid alkali metal salts, hop acid alkaline earth metal salts or combinations thereof) are combined with carrier materials (e.g., maltodextrin, cluster dextrin, corn starch, corn syrup solids, glucose, cyclodextrin, arabic gum, calaginan, inuline, partially hydrogenated soybean oil, cellulose, hydroxymethyl cellulose, hydroxyethyl cellulose, hydroxypropyl cellulose, rosin, hypomellose) to form a powder suitable for delivery. For some applications, miticides of the invention are formulated as liquids using diluents (e.g., sucrose or glucose solutions, water, juices, other aqueous solutions, water miscible solvents (ethanol, cremophor, dimethylsulfoxide (DMSO), dimethylformamide (DMF), isopropanol (IPA) or glycerol, and other solvents)) to form a solution or slurry.

A typical miticidal preparation will contain from about 1% to about 95% hop acid, where the bottom of the range is any integer between 5 and 94 and the top of the range is any integer between 6 and 95, where the hop acids are provided in a carrier (e.g., maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, hypomellose) that is suitable for use in methods of producing a product having miticidal activity. Where non-aqueous miticidal compositions are desired, the miticidal of the invention are preferably formulated with rosin or partially hydrogenated soybean oil. Such compositions may be used for the slow release of the active miticidal composition, for example, in an aqueous slurry. In still other embodiments, miticidal compositions of the invention are dispersed in cellulose powder. In each of the aforementioned embodiments, the hop acid alkali metal (e.g., sodium, potassium, lithium), alkaline earth metal salts (e.g., calcium, magnesium), or other hop acid salts are dispersed or dissolved in water, ethanol, or another diluent together with any one or more of maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, and hypomellose. The composition is then spray dried to facilitate the formation of particles less than 1 mm in size. Preferably, the conditions used for spray drying are adjusted such that the particles are at least about 1 μm, 5 μm, 10 μm, 25 μm, 50 μm, 75 μm, 100 μm, 150 μm, 200 μm, 500 μm, 1 mm, 2 mm, or 5 mm in size. The ratio of hop acids to carrier ranges between about 1:2 and 1:100. Preferred ratios include 1:2, 1:3, 1:4, 1:5, 1:6, 1:7, 1:8, 1:9, 1:10, 1:20, 1:30, 1:50, 1:75, and 1:100. Alternatively, compositions of the invention include at least about 1%, 10%, 20%, 30%, 50%, 60%, 75%, 80%, 90%, or 95% hop acid alkali metal (e.g., sodium, potassium, lithium) or hop acid alkaline earth metal salts (e.g., calcium, magnesium) in a diluent or carrier. Not all of the hop acids need be in the metal form. Anywhere between 5% and 100% of the hop acids present in the composition are in the metal form at any given time, and between 95% and 0% are present as free acids. In various embodiments, a composition of the invention contains hop acids where 90% are present in the metal form and 10% are present in the acid form; 50% are present in the metal form and 50% in the acid form; and 10% are present in the metal form and 90% in the acid form.

In preferred embodiments, the preparation includes between 1 and 95% (e.g., 1, 2, 3, 4, 5, 6, 7, 8, 9, 10, 25%, 75%, 80%, 90%, 95%) hop acids in a carrier or diluent. Alternatively, such preparations contain from about 20% to about 80% hop acids. Compositions containing alpha or beta acids are manufactured by ordinary methods. Hop acids suitable for addition to products can be formulated as ordinary tablets, capsules, solids, liquids, emulsions, slurries, fine granules or powders, which are suitable for administration to products during their preparation, following preparation but prior to storage, or at any time prior to their sale to a vendor or consumer. Lower or higher amounts than those recited above may be required. The compositions delineated herein include the compounds of the formulae delineated herein, as well as additional miticidal agents if present, in amounts effective for inhibiting mite growth or survival. Miticidal compositions of the invention may be used in virtually any application where the inhibition of a mite is desired. For example, compositions of the invention are used to prevent, reduce, inhibit, slow or stabilize the growth, proliferation, or survival of a mite.

Lower or higher doses than those recited herein may be required to effectively kill mites without adversely affecting honey bees. Specific dosage and treatment regimens are determined empirically as described herein. Compositions of the invention are also useful for preventing the establishment of an acarid infestation, for treating an established acarid infestation, and for maintaining the health of a hive previously treated for an acarid infestation.

Formulations

Hop derivatives can be provided to bees or bee hives in a number of convenient formulations. In general, strategies for dispersing a therapeutic or prophylactic agent within the hive rely on i) providing the agent in a food source (e.g., a liquid or solid food); ii) providing the agent in a composition that will induce hygienic behavior designed to remove the composition from the colony (a packet designed to be torn apart by the bees); or iii) providing the agent in a form that the bees will distribute throughout the colony (e.g., a tracking powder provided at an entrance to the hive). Formulations of the invention are used to target mites on the body of adult bees, in the brood cell, or in the hive. Desirably, the composition of the invention is active in the hive for at least forty-one days. This provides for the presence of the miticide for the entirety of the mite life cycle, which typically is completed over the course of twenty-one to thirty days. Where activity is maintained for a shorter period (e.g., seven, fourteen, twenty-one, or thirty days), repeated administration of a composition of the invention may be desired or required. Compositions that are active for longer periods (e.g., two, three, six, nine, or twelve months) are also envisioned. Such compositions may be used for the long-term treatment or prevention of a mite infestation.

Powdered Formulations

Current miticides are introduced into the beehive on plastic non-biodegradable strips that are about 1" wide, 9" long and ¼" thick. Similar means could be used for the delivery of hop derivatives. Other strip compositions include, but are not limited to, membranes, paper, plastic, and polymer strips. In one embodiment, a composition comprising a hop derivative is provided in a powdered formulation. A substrate material is coated with a powdered formulation of hop acids, and the coating is subsequently encased in a layer of a substance that is attractive to bees, such as powdered sugar. This strip is placed inside the beehive where the adult bees chew into the powdered sugar and expose the powdered hop acids. The powdered hop acids get onto the body of the adult bees, thereby contacting mites present on the adult bees and causing the mites to die. Alternatively, the hop acids are consumed by the bees and enter their hemolymph, where they are subsequently consumed by the mites, thereby causing the mites to die.

In another approach, the powdered mixture is delivered to the hive within a semi-permeable pouch that resembles a "teabag". To rid the hive of this foreign object, the bees rip up the pouch, thereby releasing the powder. The powdered hop acids get onto the body of the adult bees and are distributed throughout the hive, thereby killing (or otherwise interfering with mite proliferation or survival) mites present on the bees and inhibiting the mite infestation.

Encapsulated Formulations

In one approach, a hop derivative is provided in an encapsulated formulation (liquid or powder). Preferably, a hop derivative in liquid or powder form is encapsulated in a coating that breaks down slowly inside the beehive. The coating provides for the long-term release of the hop derivative. Preferably, the composition is released over the course of two to six weeks (e.g., two, three, four, five, six weeks). Specific materials suitable for use in capsule materials include, but are not limited to, porous particulates or substrates such as silica, perlite, talc, clay, pyrophyllite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a hop derivative or other compound specified above through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries. Encapsulation methods suitable for use in apiculture are described, for example, by Rieth et al., Journal of Apiculture Research 25(2):78-84 (1986).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of miticides. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative is placed into the hive where it subsequently contacts and kills the mites. Oil release substrates include vegetable and/or mineral oils. In one embodiment, the substrate also contains a surface active agent that renders the composition readily dispersable in water; such agents include wetting agents, emulsifying agents, dispersing agents, and the like.

Miticides of the invention can also be provided as emulsions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release.

Alternatively, miticides of the invention may also be formulated in a solid tablet and comprise (and preferably consist essentially of) an oil, a protein/carbohydrate material (preferably vegetable based), a sweetener and an active ingredient useful in the prevention or treatment of a parasitic infection in a honey bee. Methods for making such compositions are known in the art and are described, for example, in U.S. Patent Publication No. 20060008492. In one embodiment the invention provides a solid tablet and comprises (and preferably consist essentially of) an oil, a protein/carbohydrate material (preferably vegetable based), a sweetener and an active ingredient (e.g., hops α and/or β acid, or combinations or derivatives thereof) useful in the prevention or treatment of a mite infestation. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., parafins and petroleum jelly), and other water immiscible hydrocarbons (e.g., parafins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion. While the relative fraction of each portion making up the material may vary, the material should include at least a portion of carbohydrate and protein.

The tablets also contain between about 10-75% (10, 15, 20, 25, 50, 75%) by weight of a sweetener. As used herein, the term "sweetner" generally refers to both natural and artificial sweeteners. Preferably, the sweetener is a sugar such as glucose, fructose, sucrose, galactose, lactose, and reversed sugar. The sugar is preferably selected from the group consisting of granulated sugar (white sugar), brown sugar, confectioner's sugar, impalpable sugar, icing sugar, and combinations thereof. Alcohols such as glycerin and complex carbohydrates, such as starches may also be used as the "sweetener" ingredient. The sweetener is used primarily as an attractant for the insects, however the sweetener also helps to impart a granular structure to the tablets, especially when the sweetener is a sugar. As previously discussed, this granular structure permits the tablet to crumble over time upon the exertion of sufficient forces.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

Tablets according to the present invention are manufactured by mixing all of the ingredients together and then compressing the mixture into a tablet of desired shape and size for a particular application. Preferably, the tablet is discoid in shape with a diameter of between about 2-5 inches and a thickness of from about 0.5-2 inches. The pressing may be accomplished by a manual or automatic pressing device. The pressure exerted on the mixture should be sufficient so as to form the tablet into a self-sustaining body.

Methods of delivering an active ingredient to an insect according to the present invention comprise the steps of providing a solid tablet containing the active ingredient as previously described and placing the tablet in a location where the insect may come into direct contact therewith. In treating honeybees that are generally colonized in a manufactured bee hive, the tablet is preferably placed inside the hive.

Over the next several weeks after the tablet is placed into the hive, the bees chew and crumble the tablet exposing the active ingredient to the other bees. The crumbs fall through the brood box away from the honey supers. Preferably, the entire tablet is disintegrated in about 30-45 days.

Miticides of the invention can also be delivered in the form of syrups that are attractive to bees and induce feeding behavior. The syrups for use in the invention preferably comprise sugar and water. Particularly preferred are 50% w/v sucrose solutions. A liquid composition is formed by dispersing hops acids in a sugar syrup comprising 50% sucrose in water. The composition is used as a feed supplement for the bees and can be placed at a suitable location in or near a hive.

Miticides of the invention can also be delivered in packets suitable for inducing hygienic behavior in bees. Such packets are prepared by enclosing a fine powder of hops acids and sugar in a porous material capable of being torn apart by bees. Preferably, the porous material is made of waxed paper or filter paper. Suitable filter papers include those comprising abaca fibers, wood pulp and cellulose rayon fibers. If desired, the paper is coated with polyethylene mixed with copolymers, polypropylene mixed with copolymers or 100% polypropylene.

In other embodiments, miticides are prepared in a dusting composition or as a powder. Dusting compositions are typically prepared by grinding sugar to a fine powder and mixing it into the powder hops acids. Alternatively, the dusting compositions are prepared as described in Example 3 for maltodextrin, where the powder is obtained by spray drying. The skilled artisan adjusts the conditions used in the spray drying process to achieve particles or granules of a size that facilitates delivery to the bees. Desirably, the powder comprises fine particles that coat the bee and all of its body parts (e.g., joints, groove, bristles). The dusting composition can be applied directly to the top of the bee frames, to the combs within the hive, or to the interior surfaces of the hive, or may be applied directly to a bee cluster.

Alternatively, the miticides are prepared in a liquid spray composition that is formed by dispersing hops acids in any suitable liquid. Preferably, the hops acids are dispersed in water. If desired, the spray composition also includes a surfactant that allows the spray to be dispersed efficiently without clogging the spraying apparatus. The composition can be used to spray the hive interior, or the comb, or can be used to spray bee clusters directly.

In another approach, miticides of the invention are delivered in the form of a vapor. Methods for delivering such vapors to a hive are described, for example, in U.S. Patent Publication No. 20020151249.

Miticide Delivery

Devices for delivering pest control agents to bees or to a bee hive are known in the art. Such delivery devices include strips, controlled release strips, tablets, reservoirs, polymer discs, trays, and evaporation devices. If desired, the delivery device is provided in a biodegradable form. In particular, devices suitable for delivering a composition of the invention to a parasitic mite, to a honey bee, or to a honey bee hive are described, for example, in U.S. Patent Publication Nos. 20070059333; 20070026765; 20060141904; 20060009122; 20060008492; 20050095954; 20050090560; 20050048093; 20040229542; 20040077291; 20030190860; 20030044443; 20030027490; 20020182977; 20020151249; 20020094756; 20010014346 and 20020151249. Dispensing means and suitable compositions for controlled release are described in U.S. Pat. Nos. 6,843,985; 5,750,129; 4,775,534; 5,849,317; 5,348,511; 6,037,374; 7,137,864; 6,837,770; 6,820,773; 6,702,645; 6,646,014; 6,620,025; 6,595,828; 6,585,557, 6,475,061, 6,468,129; 6,277,371; 6,221,375; 6,204,283; 6,096,350; 6,037,374; 6,010,390; 5,312,622; 5,230,894; 5,227,162; 5,135,758; 5,070,091; 5,069,651; 5,023,359; 4,876,265; 4,867,731; 4,837,216; 4,682,380; and 4,299,816, which are incorporated herein by reference in their entirety.

Kits

The invention provides kits for the treatment or prevention of an acarid infestation. In one embodiment, the kit includes a composition containing an effective amount of a hop derivative in a form suitable for delivery to a site of infestation (e.g., bee hive). In some embodiments, the kit comprises a container which contains a miticide; such containers can be boxes, ampules, bottles, vials, tubes, bags, pouches, blister-packs, or other suitable container forms known in the art. Such containers can be made of plastic, glass, laminated paper, metal foil, or other materials suitable for holding miticides.

If desired the miticide of the invention is provided together with instructions for administering it to a site of infestation. The instructions will generally include information about the use of the composition for the treatment or prevention of an acarid infestation. In other embodiments, the instructions include at least one of the following: description of the miticide; dosage schedule and administration for treatment or prevention of a miticide infestation; precautions; warnings; description of research studies; and/or references. The instructions may be printed directly on the container (when present), or as a label applied to the container, or as a separate sheet, pamphlet, card, or folder supplied in or with the container.

EXAMPLES

Example 1

Hop Beta and Alpha Acids Used in Miticide Screening

Beta acids, alpha acids, and a combination of beta and alpha acids were screened for efficacy as miticides. Liquid test products containing beta acids were provided in a Beta-stab 10A® formulation (10% beta acids) hereinafter called "Betacide". Liquid test products containing alpha acids were provided in a Redihop® formulation (30% rhoisoalpha acids), Isohop® formulation (30% isoalpha acids), Tetrahop Gold® formulation (9% tetrahydroisoalpha acids), Hexahop Gold® formulation (5% hexahydroisoalpha acids and 5% tetrahydroisoalpha acids). A combination of alpha and beta acids were prepared by mixing equal parts Redihop® and Betacide. Powdered test products containing beta acids were provided by a magnesium salt formulation of beta acids. Powdered test products containing alpha acids were provided by magnesium salt formulations of Redihop®, Tetrahop Gold® and Hexahop Gold®.

Tests were carried out using the concentrations of beta, alpha, or beta and alpha acid combinations indicated in Table 1.

Specifically, in Tests 1-4: 5% beta acids as Betacide test solution, 15% rhoisoalpha acids as Redihop® test solution, and a 2.5% beta acids/7.5% rhoisoalpha acids combination was used.

In Tests 5-8, 4% beta acids as Betacide test solution, 30% rhoisoalpha acids concentration as Redihop® test solution, and a 2% beta acids/15% rhoisoalpha acids combination were used.

In Tests 9-12, 4% beta acids as Betacide test solution, 30% rhoisoalpha acids concentration as Redihop® test solution, and a 2% beta acids/15% rhoisoalpha acids combination were used.

In Tests 13-15, 30% isoalpha acids as Isohop®, 9% tetrahydroisoalpha acids as Tetrahop Gold®, and a combination of 5% tetrahydroisoalpha acids and 5% hexahydroisoalpha acids from Hexahop Gold® were used.

In Tests 16-19, 4.3% and 8.5% beta acids as a magnesium salt, and 65.5% rhoisoalpha acids as a magnesium salt of Redihop® were used.

In Tests 20-22, 25.3% tetrahydroisoalpha acids as a magnesium salt of Tetrahop Gold®, and a combination of 12.2% each of tetrahydroisoalpha acids and hexahydroisoalpha acids from magnesium salts of Hexahop Gold® were used.

Miticide Screening Assays

Tests using liquid hop products were conducted by absorbing one milliliter of test solution onto a filter paper in a Petri dish. Tests using the powdered hop products (magnesium salts) were conducted by spreading 0.5 gm of test powder evenly over filter paper in a Petri dish. Five to ten *Varroa* mites were then placed on the treated filter paper and mite survival was determined at one, four or five and twenty-four hours hour time points. Similar methods were used to evaluate the effect of the test compounds on adult honey bee survival. Adult honey bee survival was scored after twenty-two hours exposure to test product. Five to ten adult honey bees were placed in Petri dishes containing treated filter paper. Filter paper treated with water (for liquid test solutions) or cornstarch (for powdered test solutions) was used as a negative control for tests with the mites and the adult honey bees. All trials were replicated four times.

Table 1 outlines the tests and results of testing various hop products for miticidal activity.

acids and 2% beta acids killed 80% of mites. 7% mite mortality was observed under control conditions. Adult bees exposed to these same product concentrations for 24 hours showed 100% survival. These results are presented in Table 1 and FIG. 2.

In Tests 9-15 after one hour of exposure, 4% beta acids killed 20% of *Varroa* mites; 30% rhoisoalpha acids killed 13% of mites; the combination of 15% rhoisoalpha acids and 2% beta acids killed 13% of mites; 9% tetrahydroisoalpha acids killed 81% of mites; the combination of 5% tetrahydroisoalpha acids and 5% hexahydroisoalpha acids killed 100%

TABLE 1

Hop Derivatives Efficacy Against Varroa Mites of Honey Bees

| Test Number | Figure Number | Product | Active Ingredient (ai) | Product Conc. % | Test acid % Alpha | Beta | Diluent | % Mortality/Exposure Time Mites | Hours | Bees | Hours |
|---|---|---|---|---|---|---|---|---|---|---|---|
| 1 | 1 | deionized water | none | NA | NA | NA | none | 7 | 4 | 0 | 22 |
| 2 | 1 | Betacide | beta acids | 10 | NA | 5 | deionized water | 73 | 4 | 20 | 22 |
| 3 | 1 | Redihop | rhoisoalpha acids | 30 | 15 | NA | deionized water | 21 | 4 | 0 | 22 |
| 4 | 1 | Redihop + Betacide | as in test 2 + test 3 | 30 + 10 | 7.5 | 2.5 | deionized water | 43 | 4 | 7 | 22 |
| 5 | 2 | deionized water | none | NA | NA | NA | none | 7 | 4 | 0 | 24 |
| 6 | 2 | Betacide | beta acids | 10 | NA | 4 | deionized water | 87 | 4 | 0 | 24 |
| 7 | 2 | Redihop | rhoisoalpha acids | 30 | 30 | NA | deionized water | 68 | 4 | 0 | 24 |
| 8 | 2 | Redihop + Betacide | as in test 2 + test 3 | 30 + 10 | 15 | 2 | deionized water | 80 | 4 | 0 | 24 |
| 9 | 3 | deionized water | none | NA | NA | NA | none | 0 | 1 | 0 | 24 |
| 10 | 3 | Betacide | beta acids | 10 | NA | 4 | deionized water | 20 | 1 | ND | 24 |
| 11 | 3 | Redihop | rhoisoalpha acids | 30 | 30 | NA | deionized water | 13 | 1 | ND | 24 |
| 12 | 3 | Redihop + Betacide | as in test 2 + test 3 | 30 + 10 | 15 | 2 | deionized water | 13 | 1 | ND | 24 |
| 13 | 3 | Isohop | isoalpha acids | 30 | 30 | NA | deionized water | 70 | 1 | 33 | 24 |
| 14 | 3 | Tetrahop Gold | tetrahydroisoalpha acids | 9 | 9 | NA | deionized water | 81 | 1 | 0 | 24 |
| 15 | 3 | Hexahop Gold | hexahydroisoalpha acids plus | 5 | 5 | NA | deionized water | 100 | 1 | 7 | 24 |
|  |  |  | tetrahydroisoalpha acids | 5 | 5 | NA |  |  |  |  |  |
| 16 | 4 | corn starch | none | NA | NA | NA | none | 13 | 5 | ND | ND |
| 17 | 4 | MgBeta | magnesium salt of beta acids | 59.5 | NA | 4.3 | corn starch | 38 | 5 | ND | ND |
| 18 | 4 | MgBeta | magnesium salt of beta acids | 59.5 | NA | 8.5 | corn starch | 67 | 5 | 0 | 24 |
| 19 | 4 | MgRIAA | magnesium salt of rhoisoalpha acids | 65.5 | 65.5 | NA | corn starch | 7 | 5 | ND | ND |
| 20 | 5 | corn starch | none | NA | NA | NA | none | 17 | 24 | 0 | 24 |
| 21 | 5 | MgTetrahop Gold | mg salt of tetrahydroisoalpha acids | 75.8 | 25.3 | NA | corn starch | 50 | 24 | 0 | 24 |
| 22 | 5 | MgHexahop Gold | mg salt of hexahydroisoalpha acids plus mg salt of tetrahydroisoalpha acids | 36.7 | 12.2 | NA | corn starch | 50 | 24 | 0 | 24 |
|  |  |  |  | 36.7 | 12.2 | NA |  |  |  |  |  |

Notes:
NA means Not Applicable, ND means No Data

Results for the tests described in Table 1 are shown in FIGS. 1-5.

In Tests 1-4 after five hours exposure, 5% beta acids killed 73% of *Varroa* mites; 15% rhoisoalpha acids killed 21% of *Varroa* mites; and a combination of 2.5% beta acids/7.5% rhoisoalpha acids produced 43% mortality of mites. Under control conditions only 7% mite mortality was observed. The majority of adult bees survived exposure to these same concentrations of alpha and beta acids. Specifically, 100% adult bees survived exposure to rhoisoalpha acids; 80% of adult bees survived exposure to 5% beta acids; and 93% of adult bees survived exposure to the combination of 2.5% beta acids/7.5% alpha acids. These results are presented in Table 1 and FIG. 1.

In Tests 5-8 following four hours of exposure, 4% beta acids killed 87% of *Varroa* mites; 30% rhoisoalpha acids killed 68% of mites; and the combination of 15% rhoisoalpha of mites. No mite mortality was observed under control conditions. Adult bees exposed to these product concentrations for 24 hours showed 67% survival after exposure to isoalpha acids; 93% survival after exposure to the combination of 5% tetrahydroisoalpha acids and 5% hexahydroisoalpha acids; 100% survival after exposure to 9% tetrahydroisoalpha acids; and 100% survival after exposure to control conditions. These results are presented in Table 1 and FIG. 3.

In Tests 16-19, after five hours of exposure, 8.5% beta acids in the form of a magnesium salt killed 67% of *Varroa* mites; 65.45% rhoisoalpha acids in the form of a magnesium salt killed 7% of *Varroa* mites. 13% of mites died under control conditions. 100% of bees survived after 24 hours exposure to 8.5% beta acids as a magnesium salt. These results are presented in Table 1 and FIG. 4.

In Tests 20-22 after 24 hours of exposure, 25.27% tetrahydroisoalpha acids in the form of the magnesium salt killed 50% of *Varroa* mites; and a combination of 12.23% tetrahydroisoalpha acids and 12.23% hexahydroisoalpha acids both in the form of magnesium salt killed 50% of *Varroa* mites. 17% of mites died under control conditions. 100% of adult honey bees survived for 24 hours under the same conditions. These results are presented in Table 1 and FIG. 5.

Example 2

Miticidal Effect of Hop Acids in Simulated Apiary Assays

In the apiary, a bee brush was used to gently sweep bees into a ½ cup measuring cup. To prevent them from flying, the side of the bee brush was used as a lid over the cup. The 2 cup of bees was transferred to a ½ pint or pint Mason jar with a screened lid (i.e., a sugar shake jar). One jar containing a ½ cup of bees was used per container of treatment.

The containers were prepared by inserting a screen at the opening of the container and placing a cut piece of sticky board in the lid of the container. The lids were attached to the containers and the containers were turned upside down so that from bottom to top there was a lid, sticky board, and screen. A #5 rubber cork was placed in one of the two feeding holes. One jar of bees was placed briefly into the −20 freezer. The bees remained in the freezer until bee movement slowed considerably (3 to 5 minutes). At this point the bees were ready for painting using Bee paint—Testors® or another similar brand. Bees were removed from the freezer and dumped onto a metal tray. A small dot of paint was deposited on the thorax of each bee using a small paint brush. The painted bees were placed into the container by dropping them through the feeding hole until all of the bees in the jar were painted.

The desired amount of treatment was prepared and administered by quickly placing the bees in the Mason jar together with a mixture containing 2 grams of a 1:1 mixture of 52% magnesium salt of hop beta acids (Mgbeta) and cornstarch or a corn starch control. The bees in the jar were then rolled in the powder until they were completely covered in powder. Bees were then transferred to a new container where miticidal activity was assayed. During the assay, the bees were fed a 1:1 solution of sucrose with hot water and were maintained in an incubator at 32.5° C. and 60% humidity. Bee mortality was monitored daily. Feeders were replenished by removing/refilling the vials and temporarily replacing the rubber corks.

The treated bees were shaken in sugar shake to determine how many mites remained on the bees after one week. This method involves mixing ½ cup of bees with a few tablespoons of powdered sugar and shaking the bees vigorously. The loose sugar and mites are collected, and the mites are counted. The number of mites present after the sugar shake is combined with the number of dead mites that were found on the sticky boards to determine the Total Number of mites per container (T1-T4). The mortality percentages were calculated by dividing the number of dead mites on the sticky boards by the total number of mites.

| Treatment Group | Mite Mortality |
|---|---|
| T1 | 92.86% mite mortality |
| T2 | 83.33% |
| T3 | 90.9% |
| T4 (control) | 42.86% mite mortality |

The total number of mites in each treatment group, which included approximately 80 bees, ranged from 7 to 14.

Example 3

Sodium and Magnesium Salts of Hop Acids Kill Mites

Tests using the powdered hop products (magnesium salts) were conducted by spreading test powder evenly over filter paper in a Petri dish. The MgBeta test powder contained a 1:1 mixture of 0.25 g of magnesium salt of beta acids (52% magnesium beta salts of hop acids) and corn starch; thus, 26% magnesium salt of beta acids was used in the assay. The NaBeta test powder contained a 1:1 mixture of 0.25 g of sodium salt of beta acids (6.4% sodium salt of beta acids); thus, 3.2% magnesium salt of beta acids was used. *Varroa* mites were placed on the treated filter paper and mite survival was determined at one, two, three, four or five hours following exposure. Results are shown in Table 2.

TABLE 2

MITE BIOASSAY - 0.25 g Treatment

| Date | # Hours Exposure | Treatment | % Mortality |
|---|---|---|---|
| Mar. 28, 2007 | 1 | MgBeta | 4.8 |
| | | NaBeta | 15.1 |
| | | Cornstarch | 0 |
| | | Control | 0 |
| | 2 | MgBeta | 9.5 |
| | | NaBeta | 45.2 |
| | | Cornstarch | 0 |
| | | Control | 11.1 |
| | 3 | MgBeta | 14.3 |
| | | NaBeta | 45.2 |
| | | Cornstarch | 0 |
| | | Control | 11.1 |
| | 4 | MgBeta | 28.6 |
| | | NaBeta | 75.4 |
| | | Cornstarch | 0 |
| | | Control | 16.7 |
| | 5 | MgBeta | 57.1 |
| | | NaBeta | 89.7 |
| | | Cornstarch | 0 |
| | | Control | 39.2 |

Example 4

Preparation of Water-Soluble Beta Acid Sodium Salts

Step 1: Commercially available hop $CO_2$ extract (55%: Alpha acids, 30% Beta acids, 10% uncharacterized residue) (10 kg) is placed into Tank 1. $CO_2$ extracts are produced by natural carbon dioxide extraction of hops. Carbon dioxide is a natural solvent that eliminates residual solvents that typically present in hop extracts produced using hexane or ethylene chloride solvents. Food grade KOH (100 g) is dissolved in deionized water (20 L). The KOH solution is added into the Tank 1 and the mixture is stirred at 55-65° C. for 1 hour and then agitation is stopped to form two layers.

Step 2: The lower aqueous layer (15 L) is transferred into Tank 2. The crude beta acid potassium salts are cooled down to room temperature for two hours and then Celite® (diatomaceous earth) is added (0.5% wt/wt mix) for 20-30 minutes. The resulting mixture is filtered through a Buchner type filtration apparatus under vacuum.

Step 3: The filtrate (10 L) is transferred to Tank 3 and heated to 70° C. with agitation and then acidified with 30% of aqueous H₂SO₄ until the mixture reaches pH 2-3. The agitation is stopped, and the mixture is allowed to form two layers. The upper layer (5 L), which is retained, contains about 70% beta acids.

Step 4: Aqueous NaOH solution (about 9 L) is added to the upper layer (3 L) and the pH is adjusted to pH 10-10.5 at 65° C. with agitation then active charcoal (Norit A® 200 mesh) (2% wt/wt mix) is added to the solution, which is gently stirred for thirty minutes. The mixture is incubated overnight and then filtered. The filtrate is diluted with deionized water to achieve 10% beta acid sodium salts in an aqueous composition. Alternatively, the mixtures is passed over a column containing 60 mesh active charcoal.

Example 5

Preparation of Powder of Hop Beta Acid Sodium Salts

Hop beta acids are prepared as described in Example 4 with the following modification. In step 4 of Example 4, aqueous maltodextrin solution was prepared at pH 10 by mixing an aqueous beta acid sodium salts solution with maltodextrin, such that the hop acids to maltodextrin ration is 5:1 to 10:1 ratio after the filtration. The solution is dried by spray drying to obtain a pale yellow powder containing 5-10% beta acid sodium salts.

Example 6

Preparation of Hop Beta Acid Sodium Salts in 67% EtOH Solution

Beta acids are prepared as described in Example 4 with the following modification. In step 4 of Example 4, 500 ml of the aqueous solution, which contains about 30% beta acid sodium salts is mixed with 1000 ml of 100% EtOH with stirring to form 67% pale yellow ethanol solution containing 10% beta acid sodium salts.

Example 7

Preparation of Beta Acid Sodium Salts in 90% EtOH Solution 500 ml of an aqueous solution containing about 30% beta acid sodium salts is neutralized with 0.1 N H₂SO₄. The beta acid-rich fraction is precipitated out at pH 7-9. The solid is separated and washed with water three times. The solid (200 g) is dissolved into 1700 ml of 100% EtOH under stirring. 100 ml of aqueous NaOH solution (16 g of NaOH and 84 ml of water) is added to the EtOH solution under stirring to form a pale yellow clear 90% ethanol solution that contains 10% beta acid sodium salt.

Example 8

Stability Study of Hop Acids

The following samples containing hop acids were incubated under aerobic conditions at 75° C. for 0-6 days. Liquid samples were dissolved in a volume of 0.1 ml Samples
1. Beta acids rich hop extract (10%) in water (pH=5.0)
2. Powder of 10% Beta acids and 90% Maltodextrin
3. Powder of 5% Beta acid Na salts and 95% Maltodextrin
4. Powder of 10% Beta acid Na salts and 90% Maltodextrin
5. 10% beta acid Na salts in water (pH=10)
6. Hop extract with 10% hop beta acid Mg salts Following this incubation, the presence of hop acids was assayed. After incubation of 20 mg of each sample at 75° C. under aerobic conditions, the sample was dissolved into 1 ml of 70% aqueous EtOH. The solution was diluted 50 times with methanol and then 20 uL of the diluted sample was injected into a high pressure liquid chromatography (HPLC) for analysis. The HPLC conditions used were:

Temperature: 35° C.
Eluent A: 10 mM Triethylammonium acetate/water
Eluent B: 10 mM Triethylammonium acetate/acetonitrile
Gradient: Eluent B=from 30% to 90% in 20 minutes then keep B=90% for 5 minutes
Detection: 370 nm for beta acids, 254 nm for other degradation peaks
Determination: Area under the curve of three peaks (15-17 min) at 370 nm
Authentic sample: International Calibration Extract 2 from American Society of Brewing Chemists
HPLC Type: Agilent HP1100 series with diode array detector.

Samples referred to in Table 3 are described above as Samples 1-6. As shown in Table 3, alkali salts of beta acids (sample 3, 4, and 5) were more stable than the neutral form of beta acids in neutral or acidic conditions (1, 2 and 6). The results of these studies are summarized in Table 3.

TABLE 3

Stability study of hop beta acids under force conditions

| | Beta acids remained (%) Period (Day) | | |
|---|---|---|---|
| Sample | 1 | 3 | 6 |
| 1 | 52 | 20 | 0 |
| 2 | 40 | 15 | 0 |
| 3 | 100 | 100 | 98 |
| 4 | 100 | 100 | 100 |
| 5 | 100 | 90 | 90 |
| 6 | 60 | 25 | 0 |

This method provides for the rapid assessment of the chemical stability of hop acid salts relative to the degradation observed in hop acids. The degradation observed after six days at 75° C. is equivalent to the degradation that would be expected if the hop acids and salts were stored for 6 months at room temperature.

Example 9

Preparation of Rhoisoalpha Acid Salts

An inorganic salt of rhoisoalpha acids is produced using any standard method known in the art. In one embodiment, a rhoisoalpha acid is produced according to the following method.

An empty drum was placed on a scale and tared. To the drum was added 80 kg of a mixture of rhoisoalpha acids (30%) in deionized water (75 L) at room temperature. The mixture was subjected to gentle agitation to form an aqueous slurry. MgSO₄ (45 kg) was added to the slurry at one time and the agitation was continued for 5-10 minutes until the MgSO₄ was homogeneously distributed. After 10 minutes, a small sample was removed to determine whether the reaction had reached completion. This was determined using an HPLC to assay the presence of rhoisoalpha acids magnesium salt. When the reaction was complete, the mixture was removed and deionized water was added to adjust the concentration of rhoisoalpha acids magnesium salt to 15-17% having 83-85% water content. The mixture was then dried using standard methods. When the drying was completed, the flaky products were packed in aluminum coated polyethelene bags, heat sealed and stored at room temperature prior to analysis.

Example 10

Preparation of Rhoisoalpha Acids Calcium Salts

To prepare the calcium salt of rhoisoalpha acid, 300 grams of an aqueous 30% rhoisoalpha acid solution having a pH of 11 was mixed with 37 grams of $CaCl_2$-$2H_2O$, which had been mixed previously with 200 mL deionized water. This slurry was mixed until homogeneous. The slurry was then poured directly onto a drying tray and dried.

Example 11

Preparation of Rhoisoalpha Acids Lithium Salts

To prepare the lithium salt of rhoisoalpha acid, 300 grams of an aqueous 30% rhoisoalpha acid solution having a pH of 9 was mixed with 21 grams of LiOH—$H_2O$, which had been mixed previously with 300 mL deionized water. This slurry was mixed until homogeneous. The slurry was then filtered through a Buchner funnel to remove excess water and placed onto a drying tray and dried.

Example 12

Preparation of Rhoisoalpha Acids Calcium Salts

To prepare the calcium salt of rhoisoalpha acid, 300 grams of an aqueous 30% rhoisoalpha acid solution having a pH of 11 was mixed with 37 grams of $CaCl_2$-$2H_2O$, which had been mixed previously with 200 mL deionized water. This slurry was mixed until homogeneous. The slurry was then poured directly onto a drying tray and dried.

Example 13

Preparation of Rhoisoalpha Acids Potassium Salts

To prepare the potassium salt of rhoisoalpha acid, 300 grams of an aqueous 30% rhoisoalpha acid solution having a pH of 10 was mixed with 35 grams of $K_2CO_3$ which had been mixed previously with 300 mL deionized water. This slurry was mixed until homogeneous. The slurry was then poured directly onto a drying tray and dried.

Example 14

Preparation of Tetrahydroisoalpha Acid Calcium Salts

To prepare the calcium salt of tetrahydroisoalpha acid, 1000 grams of an aqueous 9% tetrahydroisoalpha acid solution having a pH of 10.5 was mixed with 42 grams of $CaCl_2$-$2H_2O$, which had been mixed previously with 100 mL deionized water. This slurry was mixed until homogeneous. The slurry was then filtered through a Buchner funnel to remove excess water and placed onto a drying tray and dried.

Virtually any hop acid alkali salt (e.g., sodium, potassium, lithium), hop acid alkaline earth metal salt (e.g., magnesium, calcium salts), or other hop acid salts may be used in the process set forth above. As set forth in the above examples, the invention provides processes for producing water soluble alkali salts or water insoluble alkaline earth metal salts of alpha acids or beta acids. Virtually any isoalpha acid, rhoisoalpha acid, tetrahydroisoalpha acid, hexahydroisoalpha acid, beta acid, hexahydrobeta acid, tetrahydrobeta acid, lupulone, colupulone, adlupulone, or derivatives or combinations thereof may be used in the processes of the invention. In one embodiment, the concentration of hop acids present in the aqueous solution ranges between 5% and 50%, inclusive. In other embodiments, the concentration ranges between 5-45% (e.g., 9%, 10%, 15%, 20%, 25%, 30%, 35%, 40%, and 45%), inclusive. In yet other embodiments, the lower end of the range is any number between 9 and 49%; and the upper end of the range is any number between 10 and 50%. The hop acids of step 4 may be dried to obtain salts any standard method or combination of methods, including but not limited to, spray drying, vacuum drying, drum drying, pan drying, window drying and freeze drying. Preferably, spray drying is used.

Compounds of the invention are prepared in a manner essentially as described above and in the general schemes. The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. Another embodiment is a compound of any of the formulae herein made by a process delineated herein, including the processes exemplified in the schemes and examples herein. Another aspect of the invention is a compound of any of the formulae herein for use in as a miticide as delineated herein.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of controlling a honey bee parasitic mite, the method comprising contacting the parasitic mite with an effective amount of a composition comprising a hop derivative, thereby controlling a honey bee parasitic mite, wherein the hop derivative comprises an alpha acid and/or beta acid.

2. The method of claim 1, wherein the contacting of the mite occurs while the mite is in contact with a honey bee.

3. A method of treating or preventing a parasitic mite infestation of a honey bee hive, the method comprising contacting the hive with an effective amount of a composition comprising a hop derivative, thereby treating or preventing a parasitic mite infestation in a honey bee hive, wherein the hop derivative comprises an alpha acid and/or beta acid.

4. The method of claim 1, wherein the parasitic mite is a *Varroa* mite or a tracheal mite.

5. The method of claim 1, wherein the composition comprises at least 2.5% alpha or beta acids.

6. The method of claim 1, wherein the composition comprises a combination of alpha and beta acids.

7. The method of claim 6, wherein the composition comprises at least 2.5% beta acid and at least 7.5% alpha acids.

8. The method of claim 1, wherein the contacting disrupts a biological function of a mite or kills the mite.

* * * * *